US 6,550,964 B2

(12) United States Patent
Guerit et al.

(10) Patent No.: US 6,550,964 B2
(45) Date of Patent: Apr. 22, 2003

(54) COVERING DEVICE FOR COVER ELEMENTS WHICH ARE MOBILE WITH RELATION TO THE OTHER AND RADIOLOGY MACHINE HAVING SUCH A COVERING DEVICE

(75) Inventors: Francis Guerit, Levainville (FR); Yann Delmas, Courbevoie (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 72 days.

(21) Appl. No.: 09/846,427

(22) Filed: May 1, 2001

(65) Prior Publication Data

US 2001/0040940 A1 Nov. 15, 2001

(30) Foreign Application Priority Data

May 9, 2000 (FR) .............................. 00 05893

(51) Int. Cl.⁷ .................................................. A61B 6/00
(52) U.S. Cl. ...................................... 378/189; 378/193
(58) Field of Search .............................. 378/189, 193, 378/197, 198

(56) References Cited

U.S. PATENT DOCUMENTS 5,069,643 A  * 12/1991 Westberg et al. ............. 440/77
5,105,455 A     4/1992 Kato et al. .................. 378/117
5,189,686 A     2/1993 Hixson ......................... 378/37
5,685,328 A  * 11/1997 Helmsderfer .................. 137/15
5,883,938 A     3/1999 Gerth et al. ................. 378/203
6,303,870 B1 * 10/2001 Nazaryan et al. ........... 174/172
6,397,882 B1 *  6/2002 Anderson .................... 137/375

FOREIGN PATENT DOCUMENTS

DE           4000826      7/1991
FR           2685058      6/1993

* cited by examiner

Primary Examiner—Drew A. Dunn
(74) Attorney, Agent, or Firm—Jay L. Chaskin

(57) ABSTRACT

Covering device comprising two rigid cover elements associated respectively with a first and with a second unit having a relative mobility, the two rigid cover elements having apertures opposite one another, and a flexible cover element having two opposite ends a first end of the flexible cover element being fixed directly to the aperture of the first rigid cover element and its second end being fixed to a rigid positioning flange whose shape is adapted to the shape of the aperture of the second rigid cover element and which comprises joining means cooperating with complementary means provided on the second unit for the flange to position the second end of the flexible cover element, in all relative positions of the two units, in such a way that the position of the second end corresponds to the position of the aperture of the second rigid cover element after placement of the latter on the second unit.

21 Claims, 4 Drawing Sheets

COVERING DEVICE FOR COVER ELEMENTS WHICH ARE MOBILE WITH RELATION TO THE OTHER AND RADIOLOGY MACHINE HAVING SUCH A COVERING DEVICE

CROSS REFERENCE TO RELATED APPLICATIONS

This application claims the benefit of a priority under 35 USC 119 to French Patent Application No. 0005893 filed May 9, 2000, the entire contents of which are incorporated by reference.

BACKGROUND OF THE INVENTION

The present invention relates to a covering device comprising two preferably rigid cover elements associated respectively with a first and with a second unit having a relative mobility, the two cover elements having apertures opposite one another, and a flexible junction between the two cover elements.

The invention in addition relates to an x-ray machine comprising a digital detection system equipped with such a covering device.

An x-ray machine comprises means for emission of an x-ray beam or radiogenic unit with an x-ray tube and a means for reception of the beam, such as a solid state detector. The means for x-ray emission and the x-ray reception means are generally supported by a mobile system having one or more axes, permitting filming at a variety of incidences.

It has been found that when an x-ray detection system using digital detection technology, an adjustment of the alignment of the detector with relation to the x-ray beam is necessary. The control system used for such alignment adjustment permits, for example, a coplanar translational motion X, Y of 20 mm, and a rotational motion of 4°.

The detector properly speaking and its support are for example enclosed in two separate covers, the cover of the detector being mobile with relation to the fixed cover of the support. Since the detector is connected to its support by mechanical connecting means, electric cables, optical fibers, tubes (water, air) and similar means, the problem arises of establishing, between the two covers mobile with relation to one another, a junction that conceals the connecting means and is esthetically pleasing as well as functional, namely impervious to the spattering of liquids, and easy to clean.

BRIEF DESCRIPTION OF THE INVENTION

In one embodiment of the invention a covering device comprises a plurality, generally two of preferably rigid cover elements associated respectively with a first and second unit having a relative mobility with respect to each other, and means for forming a junction, preferably a flexible junction, between the cover elements. The device permits simple and rapid installation and removal of one of the cover elements, installation of the latter simultaneously ensuring establishment of the junction between the cover elements.

In an embodiment of the invention an x-ray machine comprises such a covering device on its digital detection system.

The covering device according to an embodiment of the invention comprises a plurality, generally two of preferably rigid cover elements associated respectively with a first and second unit having relative mobility with respect to each other the two cover elements having apertures opposite one another, and preferably a flexible cover element having two opposite ends connected respectively to the apertures of the two rigid cover elements in such a way that the flexible cover element establishes a means for forming a junction between the two rigid cover elements in all relative positions of the two units.

A first one of the ends of the flexible cover element is fixed directly to the aperture of a first one of the rigid cover elements associated with a first one of the units and its second end is fixed to a rigid positioning flange whose shape is adapted to the shape of the aperture of the second rigid cover element associated with the second one of the units. Means for joining cooperating with complementary means provided on the second unit for the flange positions the second end of the flexible cover element, in all relative positions of the two units, in such a way that the position of the second end corresponds to the position of the aperture of the second rigid cover element after installation of the latter on the second unit.

When the two units have a relative mobility along a first and a second orthogonal translational axis, the means for joining and the complementary means advantageously are designed in such a way as to permit, when they cooperate, mobility of the flange with relation to the second unit limited to translation along a third translational axis orthogonal to the first and second axes.

When such a covering device is used for the digital detection system of an x-ray machine, comprising a detector and a support on which the detector is mounted with a relative mobility, the first rigid cover element to which the flexible cover element is fixed directly advantageously is made up of the support of the detector, and the end of the flexible cover element to which the positioning flange is fixed cooperates with the rigid cover element associated with the detector, which permits mounting and removal of the rigid cover element of the detector in simple fashion.

BRIEF DESCRIPTION OF THE DRAWINGS

An illustrative and non-limitative embodiment of the invention will be described below in greater detail with reference to the accompanying schematic drawings, wherein.

DETAILED DESCRIPTION OF THE INVENTION

Figure 1:
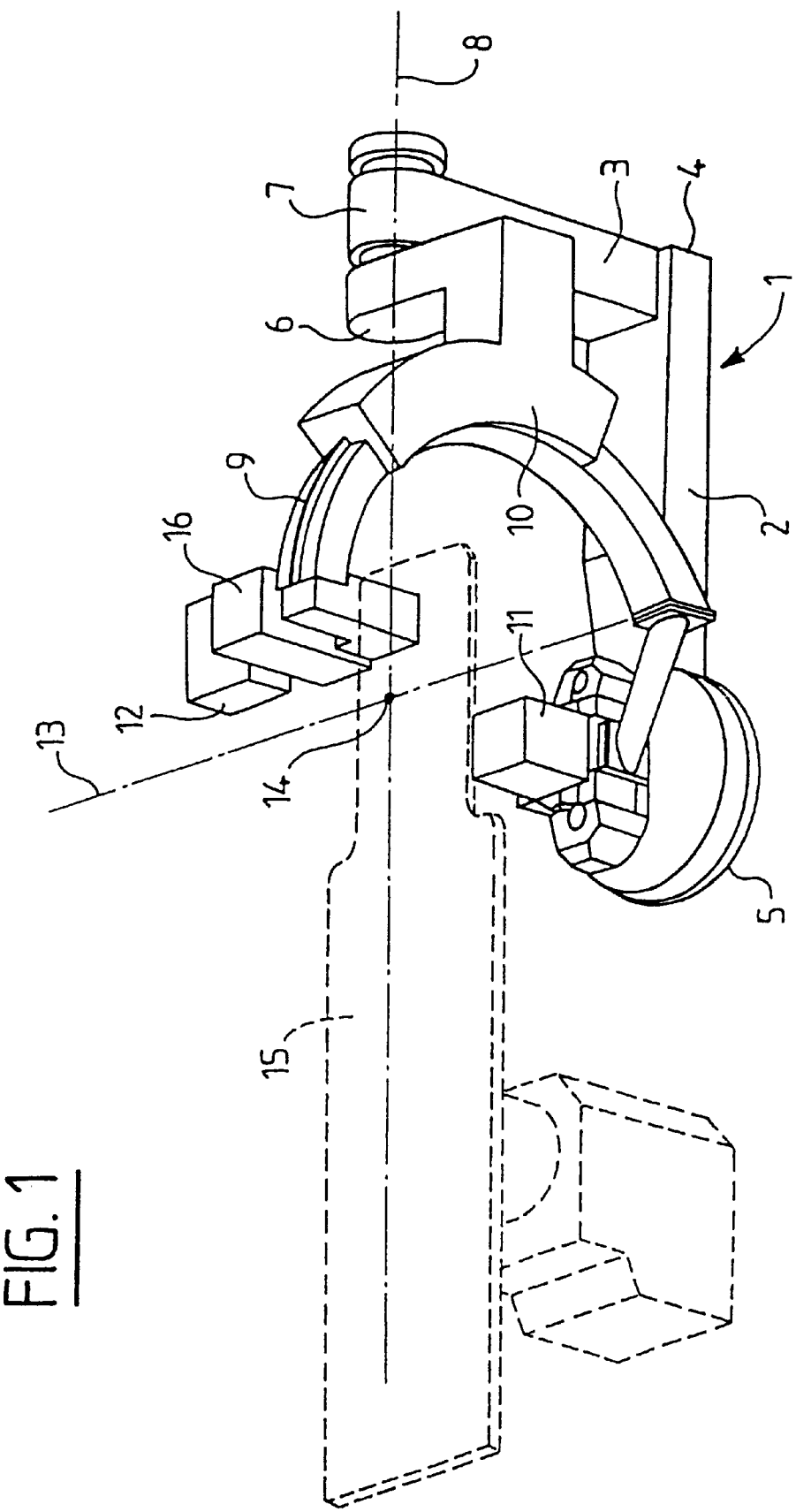
FIG. 1 is a perspective view of an x-ray machine having three axes.

As illustrated in FIG. 1, an x-ray machine comprises an L-shaped stand 1 with a substantially horizontal base 2 and a substantially vertical upright 3 at one end 4 of the base 2. At the opposite end 5, the base 2 comprises an axis of rotation parallel to the upright 3, about which the stand 1 is capable of turning. A first end of a supporting arm 6 is mounted on the top 7 of the upright 3 in such a way as to be capable of turning on a horizontal axis 8. The supporting arm 6 may have the shape of a bayonet. An arm 9, in the shape of an arc of a circle (C-shaped), is held at the other end 10 of the supporting arm 6. The C-shaped arm 9 is capable of sliding in rotational motion about an axis 13, with relation to the end 10 of the supporting arm 6.

The C-shaped arm 9 bears an x-ray tube 11 and an x-ray detector 12 in diametrically opposed facing positions. The detector 12 comprises a plane detection surface. The direction of the x-ray beam is determined by a straight line joining a focal point of the tube 11 at the center of the plane surface of the detector 12. The three axes of rotation of the stand 1, of the supporting arm 6 and of the C-shaped arm 9 are secants at a point 14. In middle position, these three axes are mutually perpendicular.

A table 15, provided for accommodating an object or a patient, has a longitudinal orientation aligned with the axis 8 in rest position. The table 15, motorized or not, can be shifted in translation along a plurality of axes.

When the detector 12 is a digital detector, it should be capable of undergoing alignment adjustment with relation to the beam of x-rays emitted by the tube 11. This is the reason why the detector 12 should be mobile with relation to its support 16 fixed on the C-shaped arm 9.

Figure 2:
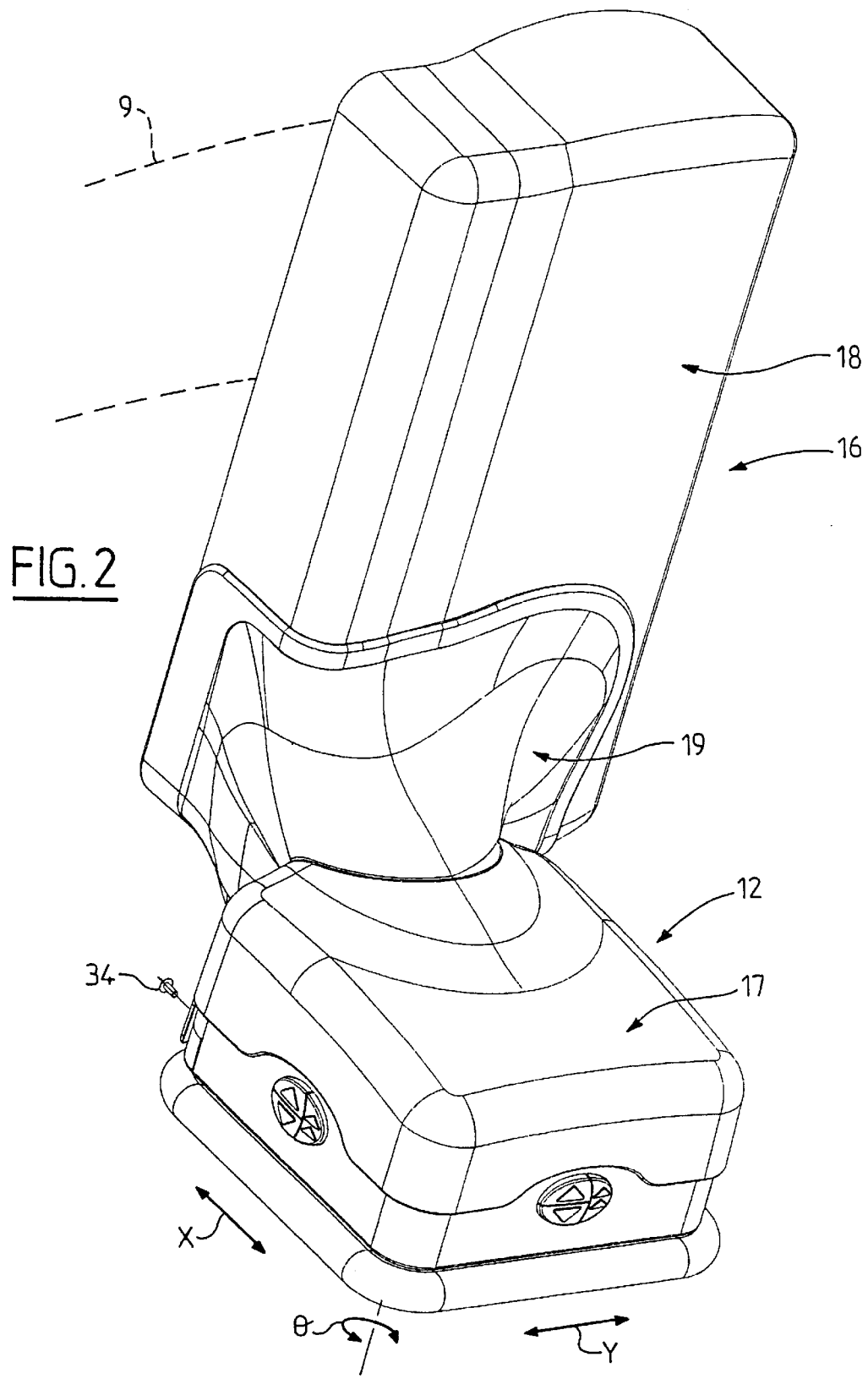
FIG. 2 is a perspective view of the x-ray detection system of the machine of FIG. 1.

As indicated in FIG. 2, the detector 12 should be capable of effecting with relation to its support 16 a coplanar translational motion along X and Y of for example 20 mm, and a rotational motion θ of for example 4°, for purposes of alignment with the x-ray beam.

Mechanical, electrical (cables, optical fibers) and fluid (water, air) or other means for connecting should be established between the detector 12 and its support 16.

According to FIG. 2, the detector 12 is covered by a rigid cover 17 and the support 16 is covered by a rigid cover 18, each of these covers being substantially parallelepipedal in shape, the cover 17 being arranged at approximately right angles to the cover 18. The two covers 17 and 18 have apertures for passage of the aforementioned means for connecting. A hollow cover element 19, which may be made of flexible material, is arranged between the two cover elements 17 and 18 in such a way as to surround the means for connecting like a sheath.

The means for joining and complementary means may comprise at least two parallel fingers cooperating by insertion with at least two parallel recesses, preferably at least two parallel fingers provided on the flange and cooperating with at least two recesses arranged on the second unit.

Figure 3:
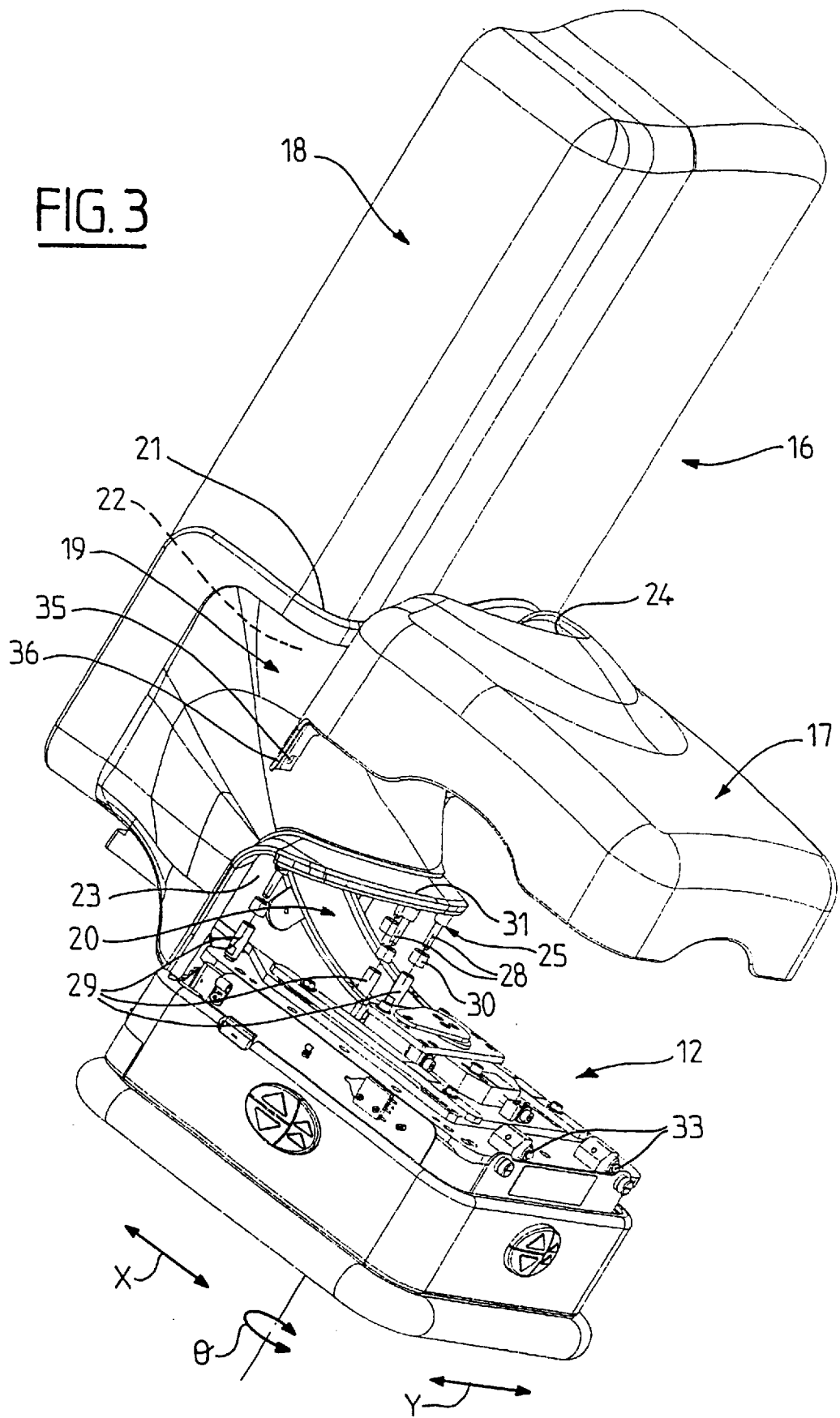
FIG. 3 is a perspective view of the system of FIG. 2, the cover of the detector having been removed.

As can be seen particularly in FIG. 3, in which the cover element 17 of the detector 12 has been removed, showing, among other things, the means for connecting 20 between the detector 12 and its support 16 and the cover element 19. One end 21 of the cover element 19 is fixed directly by for example bonding to the aperture 22 of the cover 18 of the support 16. At another end of cover element 19, at its opposite end 23 is designed to be connected to the aperture 24 of the cover 17 of the detector 12, by a rigid positioning flange 25 as represented in FIG. 4.

Figure 4:
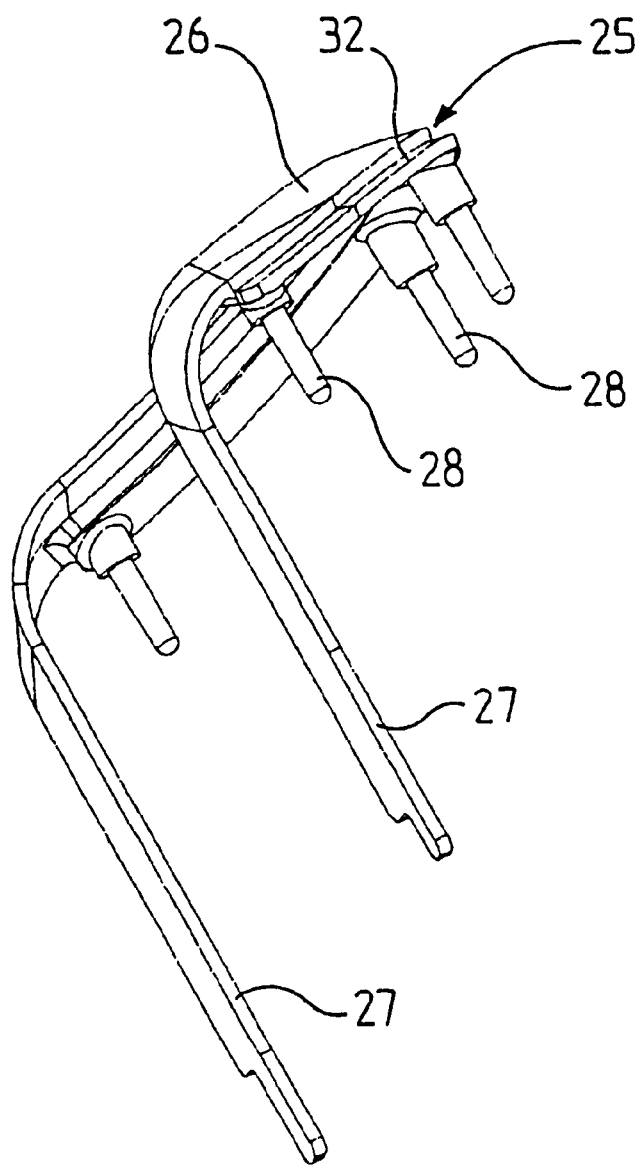
FIG. 4 is a perspective view of the positioning flange fixed to the flexible cover at the junction of the latter with the rigid cover of the detector.

The positioning flange 25, as shown in FIG. 4, is made for example of aluminum, has a general U shape, adapted to the shape of the aperture 24 of the cover element 17. The flange 25 comprises, in the example illustrated, a core 26 in an arc of a circle and two rectilinear arms 27 projecting at the ends of the core 26 in a plane substantially perpendicular to the plane of the core 26. The core 26 of the flange 25 bears a plurality of parallel fingers 28 projecting in the same direction as the arms 27. In the embodiment represented, the fingers 28 are four in number.

As shown in FIG. 3 the detector 12 comprises, for receiving the fingers 28 of the flange 25, a corresponding number of recesses 29 formed as sockets projecting upward parallel to one another.

It should be noted that in FIG. 3, the detector 12 is not represented in position of use, but in a position lowered with relation to the flexible cover element 19, in which the fingers 28 of the positioning flange 25 fixed at the end 23 of the flexible cover element 19 have not yet been inserted into the sockets 29 of the detector 12.

To improve the junction between the flexible cover element and the rigid cover element of the second unit, and in particular to permit establishment of a tight junction at this point, the flexible cover element is shaped at its second end in such a way as to surround the positioning flange on the side in contact with the second rigid cover element.

The flexible cover element preferably may be fixed by bonding to both the first rigid cover element and the positioning flange. The positioning flange advantageously may have a profiling improving fixation of the flexible cover element.

In addition, it can be seen in FIG. 3 that elastic sleeves 30, for example of flexible rubber, are threaded on the fingers 28 of the flange 25 in such a way as to be interposed between the free ends of the sockets 29 and the flange 25 in final position of the detector 12. The sleeves 30 have the effect of pushing the flange 25 and hence the flexible cover element 19, at the point of its end 23, elastically upward to lay this end of the cover element 19 against the aperture 24 of the cover element 17 when the latter is set on the detector 12, in order to make a tight junction between the two cover elements 19 and 17.

In FIG. 3, it can also be seen that the flexible cover element 19 has a part 31 that covers the core 26 of the flange 25 on the side in contact with the rigid cover element 17.

To improve fixation of the flange 25 to the flexible cover element 19, which fixation may be effected by for example bonding, the flange 25 has a profiling 32 on its core 26 (see FIG. 4), the part 31 of the cover element 19 having a corresponding profiling.

Lastly, it should be noted that, in the embodiment represented, fixation of the cover element 17 to the detector 12 is effected on one side by two ball snaps 33 on the detector 12, cooperating with a groove on the cover element 17, and on the opposite side by two screws 34 (see FIG. 2) traversing holes 35 provided in two fixing arms 36 (see FIG. 3) of the cover element 17.

The flexible cover element 19 is composed of a material that permits it to follow the motions of the cover 17 with relation to the cover 18 while retaining an impeccable appearance, in particular without forming creases. The element 19 preferably is made of silicone, advantageously of a Shore hardness of between about 40 and 60, for example a Shore hardness of 50.

The use of silicone moreover has the advantage that the element 19 not only is impervious to the spattering of various liquids that may be encountered in x-ray rooms, for example those used in vascular radiography, namely blood, liquid disinfectants, cleaning products, etc., but is also very easy to clean.

When silicone is used, it has been found that by giving the element 19 a wall thickness of between about 2 and 3 mm, for example a thickness of 2.5 mm, for a size of the order of 300×300×300 mm, the element 19 is sufficiently flexible to retain its shape in all positions that the cover 17 may assume with relation to the cover 18 under the action of the alignment system of the digital detector 12.

The element 19 of course may advantageously be dyed in bulk, either in the same color as the covers 17 and 18, or in a color contrasting with that of the covers.

It should be noted that the joining device, as represented and described in its application to the junction between two covers of an x-ray machine, may likewise be used in other fields in which the same problems arise as those described for radiology utilizing digital detector technology and involving a limited relative mobility of two rigid covers that must be joined tightly together.

Various modifications in structure and/or steps and/or function may be made by one skilled in the art without departing from the scope of the invention.

What is claimed is:

1. Covering device comprising:
   first and second cover elements associated respectively with a first and a second unit, the first and second units having a relative mobility with respect to each other along at least two orthogonal oriented axes;
   the cover elements having apertures opposite to one another;
   means for forming a junction between the first and second cover elements;
   a flexible cover element having a first end fixed directly to the aperture of the first cover element;
   the cover element, having a second end fixed to a positioning flange whose shape is adapted to the shape of the aperture of the second cover element; and
   means for joining cooperating with complimentary means provided on the second unit for the flange to position the second end of the cover element, in all relative position of orientation of the first and second units;
   in such a way that that the position of the second end corresponds to the position of the aperture of the second cover element after installation of the second cover element on the second unit.

2. The device of claim 1 wherein the first and second cover elements are rigid.

3. The device according to claim 1, wherein the cover element is fixed by bonding.

4. The device according to claim 1, wherein the first and second units have a relative mobility along a first and a second orthogonal translation axis and the means for joining and the complementary means permit mobility of the flange in relation to the second unit to translation limited along a third translational axis orthogonal to the first and second axes.

5. The device according to claim 1, wherein the means for joining and the complementary means comprise at least two parallel fingers cooperating by insertion with at least two parallel recesses.

6. The device according to claim 4, wherein the means for joining and the complementary means comprise at least two parallel fingers cooperating by insertion with at least two parallel recesses.

7. The device according to claim 1, wherein the means for joining and the complementary means comprise at least two parallel fingers on the flange cooperating by insertion with at least two parallel recesses in the second unit.

8. The device according to claim 4, wherein the means for joining and the complementary means comprise at least two parallel fingers on the flange cooperating by insertion with at least two parallel recesses in the second unit.

9. The device according to claim 1, wherein the cover element is shaped at its second end in such a way as to surround the positioning flange on the side in contact with the second cover element.

10. The device according to claim 5, wherein the positioning flange has a profiling for fixing the cover element.

11. Covering device comprising:
    two rigid cover elements associated respectively with a first and a second unit, the first and second units having a relative mobility with respect to each other along at least two orthogonal oriented axes;
    the two rigid cover elements having apertures opposite to one another;
    a flexible junction between the first and second cover elements;
    the flexible junction comprising a flexible cover element having two opposite ends;
    a first end of the flexible cover element being fixed directly to the aperture of the first rigid cover element associated with the first unit;
    a second end of the flexible cover element being fixed to a rigid positioning flange whose shape is adapted to the shape of the aperture of the second rigid cover element associated with the second unit; and
    a joining connector cooperating with a complimentary connector provided on the second unit for the flange to position the second end of the flexible cover element, in all relative positions of orientation of the first and second units, in such a way that the position of the second end corresponds to the position of the aperture of the second rigid cover element after installation of the second rigid cover element on the second unit.

12. The device according to claim 11, characterized in that the two units have a relative mobility along a first and a second orthogonal translation axis and joining connector and the complementary connector are designed in such a way as to permit mobility of the flange in relation to the second unit limited to translation along a third translational axis orthogonal to the first and second axes.

13. The device according to claim 12, wherein the joining and complementary connectors comprise at least two parallel fingers cooperating by insertion with a least two parallel recesses.

14. The device according to claim 1, wherein the joining and complementary connectors comprise at least two parallel fingers on the flange cooperating by insertion with at least two parallel fingers on the flange cooperating by insertion with at least two parallel recesses in the second unit.

15. The device according to claim 11, wherein the flexible cover element is shaped at its second end in such a way as to surround the positioning flange on the side in contact with the second rigid cover element.

16. The device according to claim 15, wherein the flange has a profiling improving fixation of the flexible cover element.

17. The device according to claim 11, wherein the flexible cover element is fixed by bonding.

18. X-ray machine comprising an x-ray detector mounted with a relative mobility on a support, wherein the detector and the support are enclosed in a first and a second respective cover elements, the second cover element of the detector being mobile with relation to the first cover element of the support, the detector and the support being connected together by means for connecting that traverse apertures of the cover elements, the means for connecting being surrounded by a cover element having opposite ends, a first end being fixed directly to the aperture of the first cover element and a second end being fixed to a positioning flange whose shape is adapted to the shape of the aperture of the second cover element and means for joining cooperating with complementary means for provided on the detector for the flange to position the second end of the cover element, in all relative positions of the detector with relation to its support, in such a way that the position of the second end corresponds to the position of the aperture of the second cover element after installation of the latter on the detector.

19. The machine according to claim 18, wherein the detector has, with relation to its support, a relative translational mobility along two orthogonal axes, and the means for joining and the complementary means are designed in such a way as to permit mobility of the flange with relation to the detector limited to translation along a third axis of translation orthogonal to the first and second axes.

20. X-ray machine comprising an x-ray detector of digital type mounted with a relative mobility on a support, wherein the detector and the support are enclosed in a first and a second separate rigid cover element, the second cover element of the detector being mobile with relation to the first cover element of the support, the detector and the support being connected together by a connector that traverse apertures of the cover elements, the connector being surrounded by a flexible cover element having two opposite ends, a first one of the ends of the flexible covered elements and a second end being fixed to a rigid positioning flange whose shape is adapted to the shape of the aperture of the second rigid cover element and which comprises a joining connector cooperating with a complementary connector provided on the detector for the flange to position the second end of the flexible cover element, in all relative positions of the detector with relation to its support, in such a way that the position of the second end corresponds to the position of the aperture of the second rigid cover element after installation of the latter on the detector.

21. The machine according to claim 20, wherein the detector has, with relation to the support, a relative translational mobility along two orthogonal axes and the joining connector and the complementary connector are designed in such a way as to permit mobility of the flange with relation to the detector limited to translation along a third axis of translation orthogonal to the first and second axes.

* * * * *